(12) United States Patent
Ren et al.

(10) Patent No.: US 9,803,294 B1
(45) Date of Patent: Oct. 31, 2017

(54) DEVICE AND METHOD FOR ELECTROSPINNING MULTIPLE LAYERED AND THREE DIMENSIONAL NANOFIBROUS COMPOSITE MATERIALS FOR TISSUE ENGINEERING

(71) Applicants: Weiping Ren, Westland, MI (US); Wei Song, Warren, MI (US); Xiao Wei Yu, Shanghai (CN)

(72) Inventors: Weiping Ren, Westland, MI (US); Wei Song, Warren, MI (US); Xiao Wei Yu, Shanghai (CN)

( * ) Notice: Subject to any disclaimer, the term of this patent is extended or adjusted under 35 U.S.C. 154(b) by 578 days.

(21) Appl. No.: 14/098,711

(22) Filed: Dec. 6, 2013

(51) Int. Cl.
*D01D 5/00* (2006.01)
*A61L 31/14* (2006.01)

(52) U.S. Cl.
CPC .......... *D01D 5/0076* (2013.01); *A61L 31/146* (2013.01)

(58) Field of Classification Search
CPC .................. D01D 5/0076; A61L 31/146
See application file for complete search history.

(56) References Cited

U.S. PATENT DOCUMENTS

| 7,993,567 B2* | 8/2011 | Scott-Carnell | D01D 5/0084 264/465 |
| 2005/0104258 A1* | 5/2005 | Lennhoff | D01D 5/0076 264/465 |

OTHER PUBLICATIONS

"Bionic electrospun ultrafine fibrous poly(lactic acid) caffolds with a multi-scale structure"; Kai Zhang, Xuefen Wang, Dazheng Jin, Yin Yang, and Meifang Zhu Biomedical Materials 4 (2009) (pp. 1-6).*

"Increasing electrospun scaffold pore size with tailored collectors for improved cell penetration" Cedryck Vaquette, Justin John Copper-White Acta Biomaterialia 7 (2001) 2544-2557.*

* cited by examiner

*Primary Examiner* — Kevin R Kruer (57) ABSTRACT

The present invention relates to a device for preparing three dimensional (3D) nanofibers (blended or coaxial) materials by electrospinning. An automatic nanofiber collector device is used to control the porosity, pore size, crystallinity, geometry, the layer number and thickness of formed nanofibers. The automatic nanofiber collector device includes: (1) a collector platform; (2) a non-conductive device used to fix the collector device; (3) a plurality of electro-conductive wires or needles being pierced through the collector platform with various heights, and (4) the ends of the needles (at bottom) are wired and controlled by a microcontroller, providing forward, stand and backward movements for attached needles. The desired 3D nanofiber scaffold structures can be tailored by the micro-stepping programmable motor controller by changing the pattern and velocity of needle movement, generalized or selective needles movements, as well as intermittent versus continuous movement.

5 Claims, 8 Drawing Sheets

Illustration of an automatic nanofiber collector device

Figure 1. Illustration of an automatic nanofiber collector device

Figure 2 Multiple rounds (5, 10 and 20) for building 3D nanofibers on automatic nanofiber collector Figure 3  Preparation of 3D nanofiber composite scaffold by co-electrospinning.

Figure 4. SEM morphology of 3D nanofiber scaffold. (b, c, d) on the dissection surface, and (e, f, g) morphology of nanofibers on actual scaffold surface.

Figure 5. Micro CT analysis of 3D and 2D nanofiber scaffold. 3D rendering of the (a, c) 3D and (b, d) 2D scaffolds. (e) pore size distribution and (f) interconnectivity.

Figure 6. DSC analysis of (a) 2D and (b) 3D nanofibers scaffolds showing the presence of melting and recrystallization.

Figure 7. MC3T3 cell adhesions on 3D nanofiber scaffold. (a) Illustration of cell seeding and migration process. (b, c) 3D reconstruction of a confocal z-stack generated from scanning result of 3D scaffold cultured with cells Figure 8. MTT assay of MC3T3 cells grown on 3D PCL nanofibers for 7 days (n=3). MTT activities were much higher in nanofibers collected with needle movement than traditional NFs. ** p<0.01 vs. control, * p<0.05 vs. control.

DEVICE AND METHOD FOR ELECTROSPINNING MULTIPLE LAYERED AND THREE DIMENSIONAL NANOFIBROUS COMPOSITE MATERIALS FOR TISSUE ENGINEERING

CROSS-REFERENCE TO RELATED APPLICATIONS

This application claims priority to U.S. Provisional Patent Application Ser. No. 61/797,817, entitled "Device and method for electrospinning multiple layered and three dimensional nanofibrous composite materials for tissue engineering" filed on Dec. 12, 2012, which is incorporated herein in its entirely.

FIELD OF INVENTION

The present invention relates to a device for preparing three dimensional (3D) nanofibers (blended or coaxial) materials by electrospinning. An automatic nanofiber collector device is used to control the porosity, pore size, crystallinity, geometry, the layer number and thickness of formed nanofibers. This new nanofiber collection device can be used alone or by simultaneous incorporating of other biomaterials, biomolecules and viable cells to form desired 3D nanofiber matrix composites.

BACKGROUND ART

Nanofibers are ultrafine filament substances with seemingly unlimited marketplace applications. These highly versatile filaments can be produced artificially though electrospinning—a process that uses an electrical charge to draw nanofibers from a polymer solution. The standard electrospinning device setup consists of a spinneret (typically a syringe needle) connected to a high-voltage (5 to 50 kV) direct current power supply, a syringe pump, and a grounded collector. A polymer solution is loaded into the syringe and this liquid is extruded from the needle tip at a constant rate by a syringe pump.

Conventional electrospinning procedure results in dense two-dimensional (2D) fibrous mat that are collected over time, giving rise to compact structure with small pore size that inhibits cell infiltration and proliferation[1,2]. These densely packed layers of nanofibers have only a superficially porous network and form a sheet-like microstructure. This unavoidable characteristic restricts cell infiltration and growth through the entire layers of nanofiber scaffolds.

In order to architecture three-dimensional (3D) nanofibrous scaffolds with lower density and larger pore size, numerous approaches have been attempted[3,4], including the incorporation of nanoparticles, using larger microfibers, or removing embedded salt or water-soluble fibers to increase porosity.

Some basic parameters that govern electrospinning process, such as electric charge, external force on spinneret jet, magnetic field[5] have been investigated for promoting 3D fibers architecture. However, it has been demonstrated that collection method acts most effectively on constructing 3D fibers and manipulating elaborate fibrous structure[6]. Advanced collection techniques, such as wet electrospinning[7], rolling or stacking collectors[8-10], and yarn[11] have shown to be eligible for 3D nanofiber fabrication. From designing various geometrical collectors instead of the conventional parallel-plate collectors, it's possible to produce 3D nanofibers scaffold in certain shapes.

Overall, all current strategies to create electrospun scaffolds collect nanofibers in an unfocused, planar manner, which causes subsequent layers to adopt a densely packed network and prevents the formation of three dimensional structures with good stability. To overcome this limitation, we invented an automatic nanofiber collector device to control the porosity, pore size, crystallinity, geometry and the number of the layers and/or thickness of formed nanofibers.

The design of the automatic nanofiber collector device is consists of (1) a collector platform; (2) a non-conductive device used to fix the collector device; (3) a plurality of electro-conductive wires or needles being pierced through the collector platform with the same or various heights, and (4) the ends of the needles (at bottom) are wired and controlled by a microcontroller, providing forward, stand and backward movements for attached needles.

This automatic nanofiber collector device is specially designed by embedding an array of electro-conductive needles in a flat surface. The terminals of the needle are wired and controlled by micro-steppler controller. The micro-stepper is programmed to control individual needle movement (forward, backward and still at desired moving velocity).

Nanofibers are allowed to accumulate throughout the electrospinning process and then removed manually or automatically. The mechanism behind nanofiber accumulation is that a corona discharge is formed during electrospinning when the heights of pierced needles varies, enabling the gradual built-up of electrospun nanofibers on the collector and eventual formation of 3D bulk nanofiber scaffold.

The desired structure of the 3D nanofiber scaffold can be tailored by the micro-stepper motor controller by changing the pattern and velocity of needle movement, generalized or selective needles movements, as well as intermittent versus continuous movement.

This automatic nanofiber collection device can be used alone (single electrospinning) or by simultaneous incorporating (spray, co-electrospinning or 3D plotting/plasma spraying or other applicable loading methods) of other biomaterials (biopolymers, bioceramics, bio-conjugates, etc.), biomolecules, ions (trace elements), viable cells (stem cells or differentiated cells), to form desired 3D nanofiber matrix composites (Sandwich, layer-by-layer, gradient models, and thereof).

The potential application of this new technology includes, but not limited to, the tissue engineering of soft and hard tissues, and controllable drug delivery.

The desired 3D structure of nanofiber scaffold can be tailored by changing the pattern and velocity of collector surface needle movement programmed by a micro-stepped motor controller.

One of the unique characters of automatic nanofiber collector device is that a corona discharge effect is applied as the mechanism of collecting nanofibers throughout the heads of the needles. By controlling the movement of the aligned needles, nanofibers continue to build up along the needle heads concurrently. This new method extended the application of the electrospinning techniques in providing 3D nanofibrous scaffold in both soft tissue and bone tissue engineering, among other potential biological or industrial applications.

Ho-Wook Jun et al., (U.S. Pat. No. 0,250,308 A1) disclose the use of different geometric collectors with fixed electrodes to produce 3D electrospun nanofibers. The inventors focus on designing of geometries of non-conductive distal end plate without considering the movements of electrodes.

Mohammadi Yousef, et al., (Euro Pat. No. EP2045375 (B1)), disclose the design of rotating collector, which consists of multiple electrodes-formed cylindrical cages, to produce 2D or 3D electrospun nanofibers with alignment.

Vince Beachley et al. (U.S. Pat. No. 7,828,539) disclose the design of two parallel conducting plates with rotating tracks to align the fibers and distribute the fibers into 3D fiber mesh.

In most tissues, cells are embedded in the entangled extracellular matrix network (ECM). Proper cell phenotype is of particular importance in regulating matrix biosynthesis and remodeling. It is evident that spatial arrangement of cells embedded in ECM has a great effect on the phenotypic fate of these cells. The interactions between cells and cell-matrix both play an important role by regulating different gene expression. The micro scale contact and communication between cells and cues from the matrix cause sequential intracellular events to influence cellular behavior.

Fabrication of 3D nanofiber scaffold with programmed spatial control of cell deposition is challenging. Many efforts have been made in recent years in developing and testing printing techniques including those based on laser pulses, inkjets and other more novel approaches[12,13;14,15]. Valve-based printing techniques are one of the newest additions to this list and have the advantage of being one of the gentlest techniques for printing any number of cells but, as with all other nozzle-based techniques, clogging is potentially an issue[16;17].

We developed a new cell printing platform that is capable of depositing cells with precise quantity and high cellular viability. The combined methods of electrospun 3D nanofiber matrix with layer by layer based cell deposition systems were used for the controllable and repeatable creation of uniform 3D nanofiber matrix with desired multilayer deposit of viable cells. It can be a single nozzle system[18] or dual nozzle system[19].

DETAILED DESCRIPTION OF THE INVENTION

Example 1

Description of Automatic Nanofiber Collector Device

Figure 1:
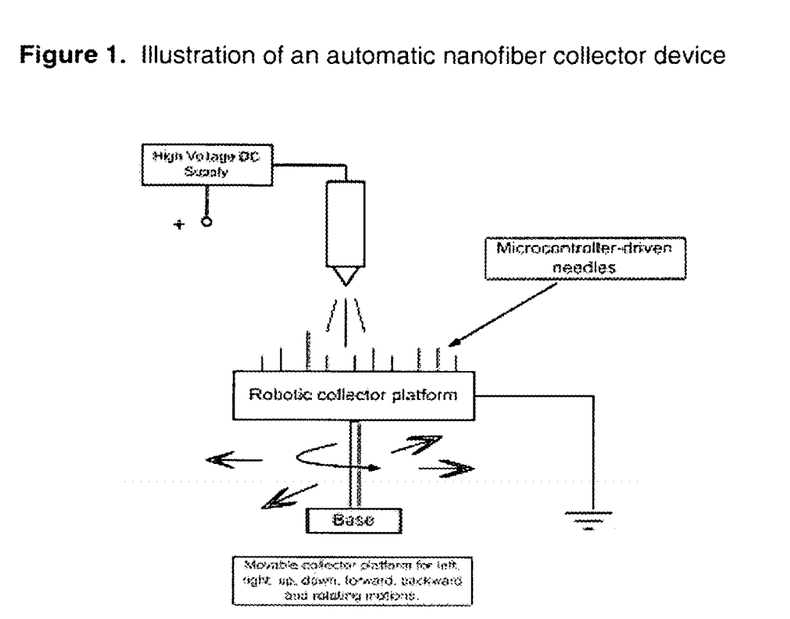
FIG. 1. Illustration of an automatic nanofiber collector device

The design of the automatic nanofiber collector device is shown in FIG. 1. This nanofiber collector is consists of (1) a collector platform; (2) a non-conductive device used to fix the collector device; (3) a plurality of electro-conductive wires or needles being pierced through the collector platform with various heights, and (4) the ends of the needles (at bottom) are wired and controlled by a microcontroller, providing forward, stand and backward movements for attached needles.

This device is specially designed by embedding an array of 3.0 cm long stainless needles in a flat surface (diameter: 3 cm, shell thickness 0.2 cm; Fibre Craft, USA). The terminals of each needle are wired and controlled by microcontroller via a stepper motor. The micro-controller is programmed to control individual needle movement (forward, backward and still at desired moving velocity, 0-10 mm/per minute). The needles are placed at 1 cm intervals radiating from the center of the collector surface in four equidistant directions. Nanofibers are allowed to accumulate throughout the electrospinning process and then removed with a glass rod.

The mechanism behind nanofiber accumulation is that a corona discharge is formed during electrospinning when the heights of pierced needles vary, enabling the gradual built-up of electrospun nanofibers on the collector and eventual formation of 3D bulk nanofiber scaffold. The desired structure of the 3D nanofiber scaffold can be tailored by the stepper motor controller by changing the pattern and velocity of needle movement, generalized or selective needles movements, as well as intermittent versus continuous movement. The desired 3D structure of nanofiber scaffold can be tailored by changing the pattern and velocity of needle movement on the collector surface programmed by a stepper motor controller.

Figure 2:
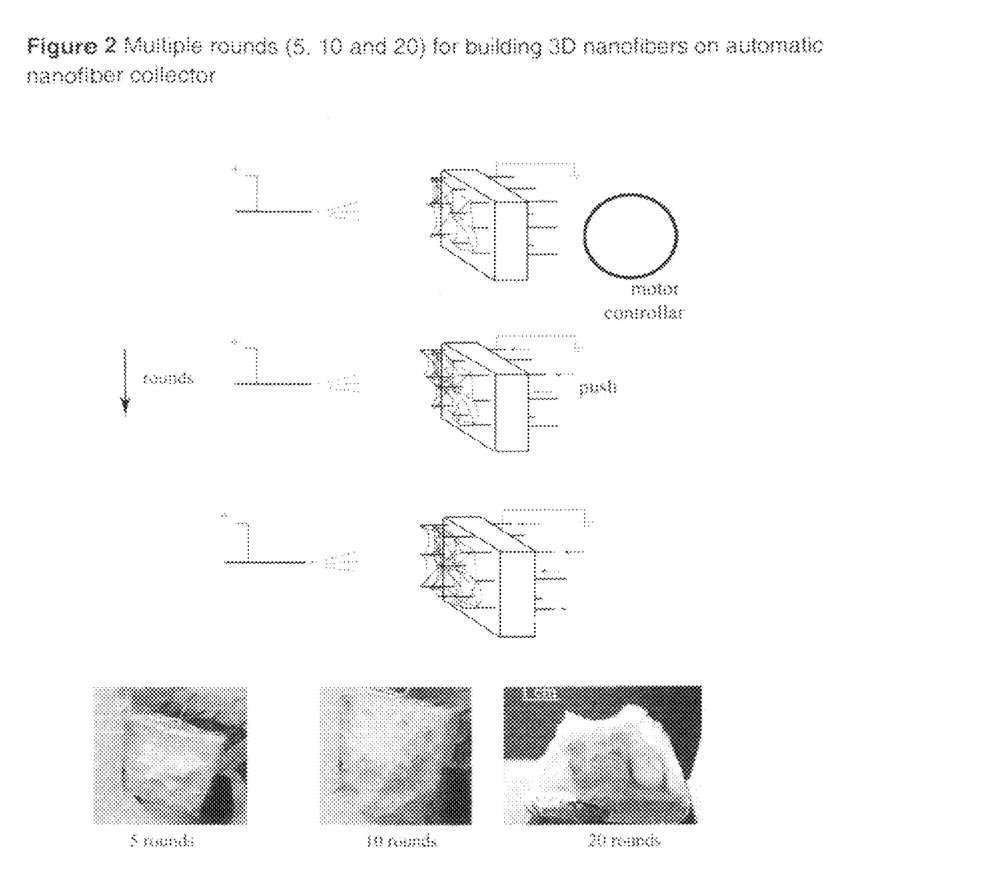

FIG. 2 shows the illustration in cross-sectional view of electrospun nanofibers deposited along needles and platform during electrospinning. The newly formed nanofiber layer can be pull to the downside of needle heads, so the free needle heads arrays are ready to receive a new layer of formed nanofibers. In a cycle, the 3D nanofiber can be formed along the needle with the desired nanofiber thickness.

The morphology of nanofiber can be further controlled by additional parameters, such as the density of needles array in a defined area, the difference of needle height among the needle array, the thickness and nature of electro conductive needles or wires, the speed or patterns of needle movement (say the stop, forward and backward movement of single needle, a bound of few needles or entire needle arrays). The structure or shape or morphology of each needle or wire can be homogenous or highly diversified.

One exemplary method of forming a 3D structured nanofibrous mesh, among others, includes: the desired nanofiber thickness can be controlled by the layer by layer deposition through programmed electrospinning of formed nanofiber scaffolds. During the transition layer, we can co-electrospray different molecular materials forming sandwich nanofiber structures.

One exemplary structure, among others, includes: an uncompressed fibrous mesh including a fiber, wherein the uncompressed fibrous mesh has a volume that is about 50 to 1800 cm$^3$, wherein the fiber occupies about 5 to 20% of the volume of the uncompressed fibrous mesh, wherein the thickness of the nanofiber sheet can be about 10-1000 um.

Example 2

Preparation of 3D Nanofiber Composites Scaffolds by Co-Electrospinning

Figure 3:
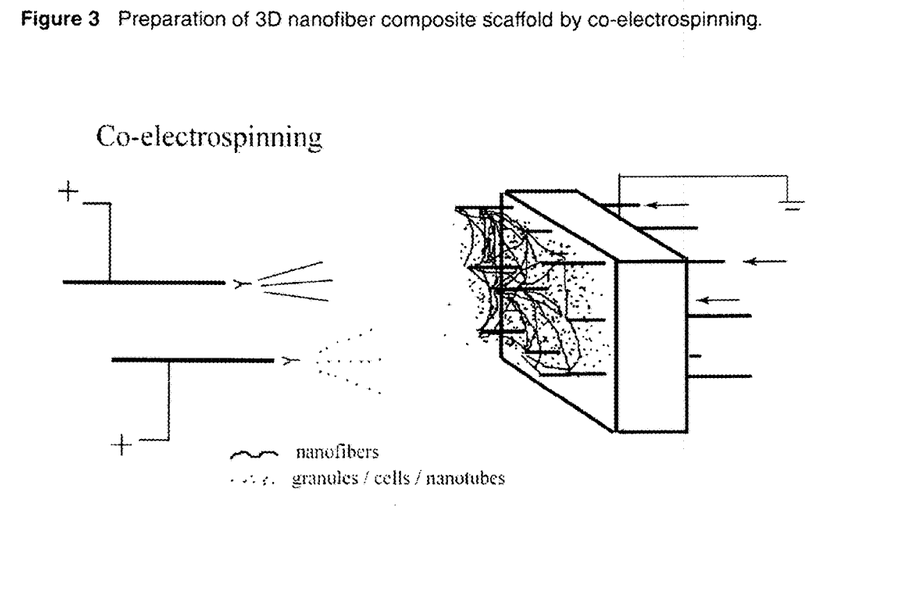

FIG. 3 illustrates the preparation of 3D nanofiber composite scaffold by co-electrospinning. The electrospun nanofiber mesh could wrap granules, cells, nanotubes by loading of biomaterials simultaneously or separately during electrospinning. Alternatively, various types of tissue scaffolds with desired shape can be made by compressive modeling or other molding technology for tissue repair.

This automatic nanofiber collection device can be used alone (single electrospinning) or by simultaneous incorporating (spray, co-electrospinning or 3D plotting/plasma spraying or other applicable loading methods) of other biomaterials (biopolymers, bioceramics, bio-conjugates, etc.), biomolecules, ions (trace elements), viable cells (stem cells or differentiated cells), to form desired 3D nanofiber matrix composites (Sandwich, layer-by-layer, gradient models, and thereof). The potential applications of this new technology include, but not limited to, the tissue engineering of soft and hard tissues, and controllable drug delivery.

Example 3

Electrospinning of PCL Nanofibers

A Polycaprolacton (PCL) mixture (0.2 mg/mL) was prepared by dissolving PCL into chloroform through overnight homogenization. 10 mL of dimethylformamide (DMF) was then added to the mixture and stirred for 3 hours until it was evenly homogenized. For imaging purpose, Calcein fluorescent labeling dye (8 µg/mL) was mixed with the PCL solution to finalize as PCL-calcein solution for electrospinning. The solution was then loaded into a syringe (5 mL, B-D Scientific, Franklin Lakes, N.J.), which made a connection with high purity tubing (INDEX Health and Science, Oak Harbor, Wash.). Attached to the end of the tubing was a blunt tipped (B-D Scientific) 26 $G^{1/2}$ needle (0.6 mm inner diameter). The entire syringe, tubing, needle system was attached to a syringe pump (R-100E, Razel Scientific Instruments, St. Albans, Vt.) with a setting flow rate Q. The needle tip was connected using alligator clips to a high voltage supply (ES40P, Gamma High Voltage Research Inc., Ormond Beach, Fla.).

The electrospinning process was performed at certain settings which are as follows: Flow Rate (Q)=7.8 µL/min, Voltage (V)=19-20 kV, and a needle tip to plate collector distance=10 cm. A static immobile collector plate was utilized as opposed to a spinning collector. The collector was a 3×3×1 cm foam plate wrapped in aluminum foil and pierced by 18 forward-reverse movable needles. The needles were placed in the concentric squares, evenly distributed along the plate. Eleven rounds of electrospinning steps were conducted in the dark at 20 min/round for performing the construction of 3D scaffold. Embedded needles were moved forward and backward at every round as needed to focus fiber distribution on certain locations. Collected 3D scaffolds were placed in aluminum covered petri dishes and stored in dark.

Example 4

Figure 4:
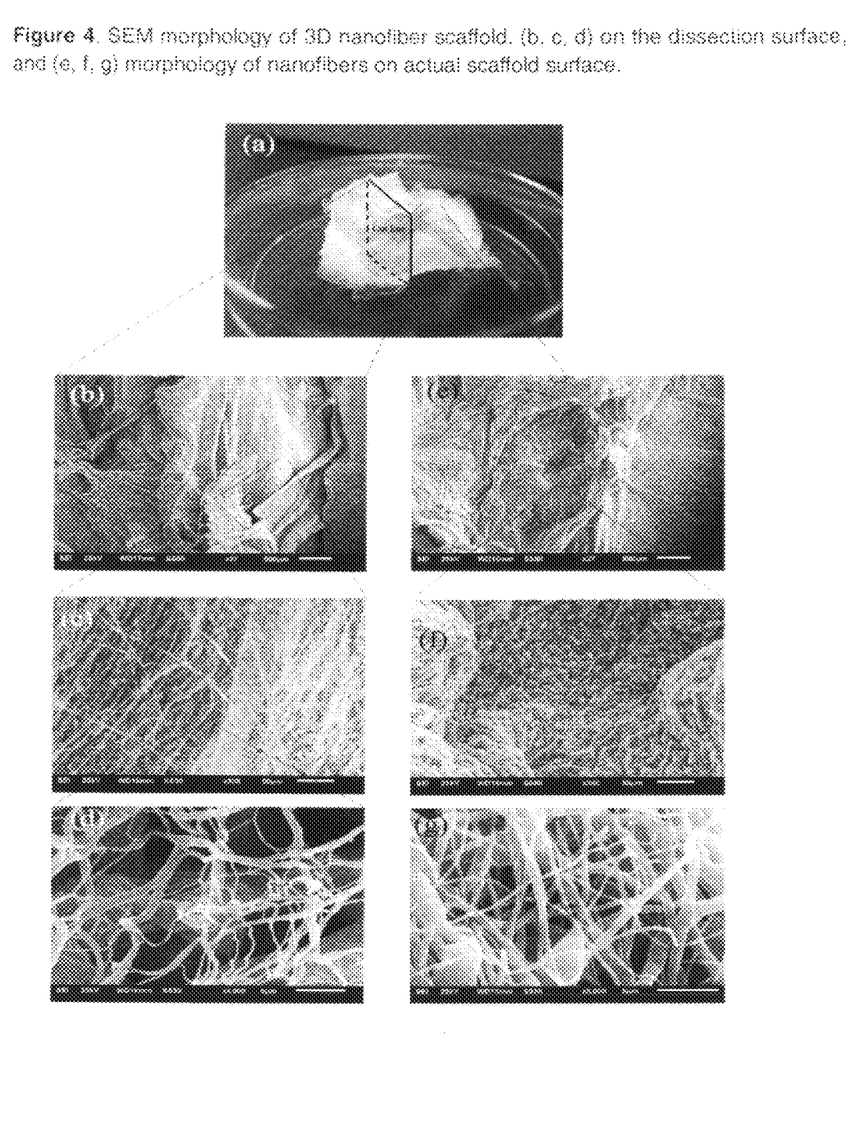
FIG. 4. SEM morphology of 3D nanofiber scaffold. (b, c, d) Morphology of nanofibers on the dissection surface, and (e, f, g) morphology of nanofibers on actual scaffold surface.

3D PCL Nanofiber Morphology and Porosity Measured by Scanning Electron Microscopy A PCL 3D nanofiber scaffold was firstly gold-coated (Gold Sputter, EFFA Coater, Redding, Calif., USA) and the morphology of the nanofibers was characterized by Scanning electron microscope (SEM) (JSM-6510LV-LGS, MA, USA). Morphologies were viewed at a 25 kV accelerating voltage. (FIG. 4)

SEM showed that a three-dimensional scaffold includes electrospun nanofibers with a similar diameter but larger pores and less dense structure compared to the traditional electrospun scaffolds. Packed multi-layers of fiber sheets can be observed in the internal architecture of 3D scaffold (FIG. 4 (b)). Each layer consists of a loose fiber-mesh surface of meso-porous structure with pore size varied from several to hundred microns (FIG. 4 (c, d)). The morphology of 3D scaffold surface shows a single rough fiber sheet (FIG. 4 (e)). Denser structure can be revealed on surface layer (FIG. 4 (f)) and smaller pore size was also found (FIG. 4 (g)). We believe that the increased pore sizes in the 3D scaffold allows cells enough room to deeply infiltrate the scaffold, while still providing the needed interconnectivity to bridge the pores across multiple nanofibers.

Example 5

Micro-CT Analysis of 3D PCL Nanofiber Morphology and Porosity

Each nanofiber scaffold was scanned with the Scanco VivaCT 40 using a voltage of 45 kVp and a current of 177 µA at 10 µm resolution. A cylindrical volume of interest with 785 slices was selected for 3D scaffold and 400 slices were selected for the homogeneous scaffold. The morphology of the scaffolds was determined using a software from the manufacturer to measure the average wall thickness (Tb.Th), average pore size (Tb.Sp), porosity, pore size distribution and interconnectivity.

Figure 5:
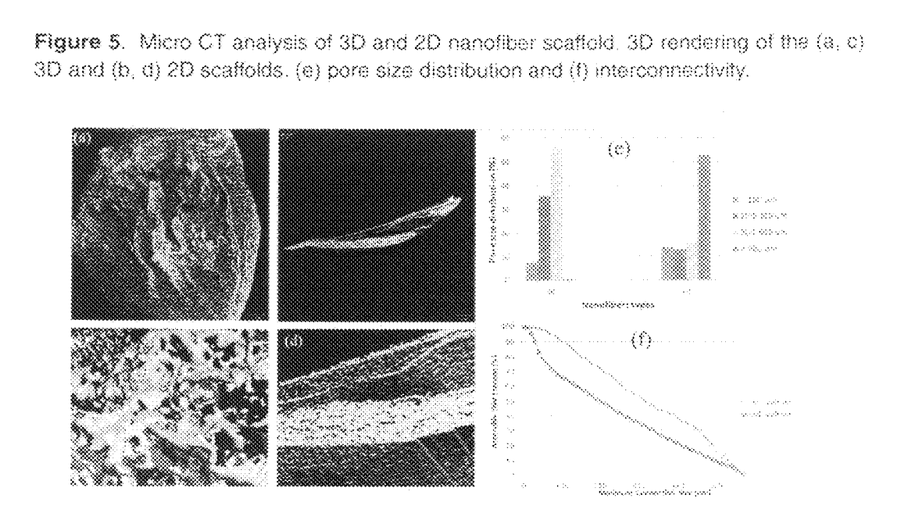
FIG. 5. Micro CT analysis of 3D and 2D nanofiber scaffold 3D rendering of the (a, c) 3D and (b, d) 2D scaffolds. (e) pore size distribution and (f) interconnectivity.

From the reconstructed 3D nanofiber images (FIG. 5, (a, b)), it can be seen that 3D nanofiber scaffold showed a bulk shape while 2D nanofiber scaffold showed dense sheets shape. The much higher volume/weight ratio (39.5 $cm^3/g$) of 3D nanofiber scaffold demonstrates the less dense structure in comparison of 2D nanofiber scaffold. The pore size distributions of 3D and 2D nanofiber scaffold were majorly around 100-600 µm and >600 µm, respectively (FIG. 5, (e)). This result indicates that evenly distributed smaller-pores (<600 µm) are mostly found in 3D nanofiber scaffold rather than in 2D nanofiber scaffold. Another critical parameter for porous nanofiber scaffold is interconnectivity. The percentage of pores that were connected to the outside environment through openings (<525 µm) of 3D nanofiber scaffold is higher than 2D nanofiber scaffold (FIG. 5, (f)), which indicates higher interconnectivity. From magnified images (FIG. 5, (c,d)), 3D nanofiber scaffold showed higher amount of interconnective pores and isotropic structure.

Example 6

Differential Scanning Calorimetry (DSC) of 3D PCL Nanofibers

The calorimetric measurement was performed on a Q2000 differential scanning calorimeter (TA Instruments Inc., New Castle, DL) in a dry nitrogen atmosphere. The instrument was calibrated with standard Indium. All samples (about 8 mg) were heated to 80° C. and held for 5 min, and then quenched to the room temperature. The DSC thermograms were recorded at a heating and cooling rate of 5° C./min. The crystallization temperatures (Tc) and the melting temperatures (Tm) were taken as the temperatures at the maximum and the minimum of both endothermic and exothermic peaks, respectively.

Figure 6:
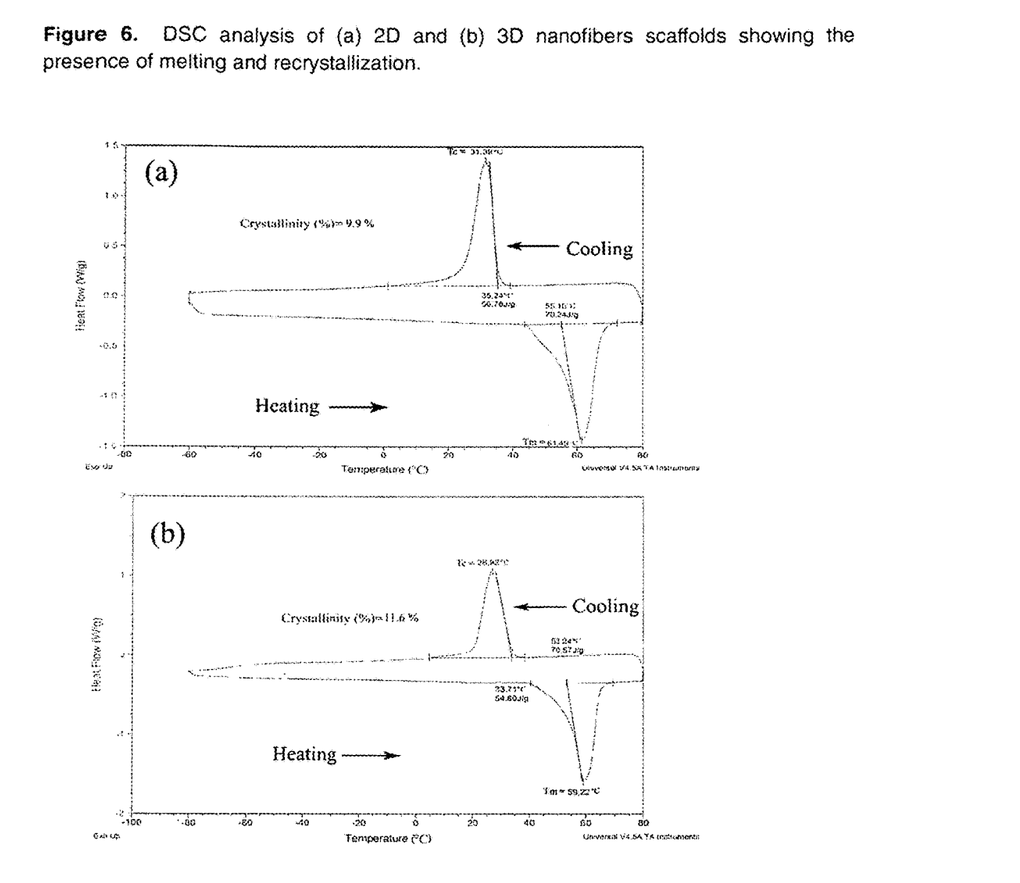
FIG. 6. DSC analysis of (a) 2D and (b) 3D nanofibers scaffolds showing the presence of melting and recrystallization.

As shown in FIG. 6, both 2D and 3D nanofiber scaffold showed Tm at about 60° C., whereas 3D nanofiber scaffold showed lower Tc than 2D nanofiber scaffold. The percent crystallinity of both 2D and 3D PCL nanofiber scaffolds, Xc, was calculated using the observed enthalpy of fusion of 100% crystallized PCL in the following equation:

$X_c = (\Delta H_f - \Delta H_c)/\Delta H_f° \times 100\%$, where $X_c$ is the percent of crystallinity. $\Delta H_f$ and $\Delta H_c$ are the enthalpy of fusion and crystallization of PCL, respectively. $\Delta H_f°$ is the fusion enthalpy of perfectly crystallized PCL, and it has been reported to be 136 $J \cdot g^{-1}$. Accordingly, the percents of crystallinity of 2D and 3D nanofiber scaffolds were calculated as 9.9% and 11.5%, respectively. Apparently, both 2D and 3D nanofibers showed low crystallinity. 3D nanofibers with slightly higher crystallinity might due to the collecting needles that enhanced crystallization along fibrous direction. The higher percent of crystallinity also decreased the Tc to lower level. Thus, the lower HDT of 2D nanofibers can be interpreted by lower crystallinity from DSC analysis.

Example 7

Growth of MC3T3 Cells on 3D PCL Nanofibers

Cell Culture

3D PCL nanofiber scaffolds were placed into 5 mm petri-dish. Murine MC3T3-E1 pre-osteoblast cells were cultured in α-MEM (Invitrogen) supplemented with 10% fetal bovine serum (Invitrogen), 10 mM β-glycerophosphate (Sigma), and a 1% (v/v) antibiotic mixture of penicillin and streptomycin at 37° C. in a humidified incubator with 5% $CO_2$. MC3T3-E1 cells were seeded at a density of $1.5 \times 10^4$ cells/dish (5 mm petri-dish) onto the 3D scaffold surfaces.

Confocal Laser Scanning Microscopy (CLSM)

To better show the cell-nanofibers interaction, cells attached on the scaffold surface were stained and observed under CLSM. For preparing the samples for the CLSM, the scaffold was washed three times by PBS. Cells were labeled by DiI cell-labeling solution (Invitrogen) at 37° C. for 15 min. DiI is a lipophilic membrane stain that diffuses laterally to stain the entire cell. Samples were then washed three times using PBS and soaked in petridish using warmed PBS. The fluorescent images were obtained via a confocal laser-scanning microscope (LeicaTCS SP II, Leica) under 10× objective. The slices of the scaffold from z-stacks were captured and reconstructed using Volocity software (PerkinElmer, American). The reconstructed 3D images were used to demonstrate the cell migration and proliferation along the internal structure of the 3D scaffold.

Figure 7:
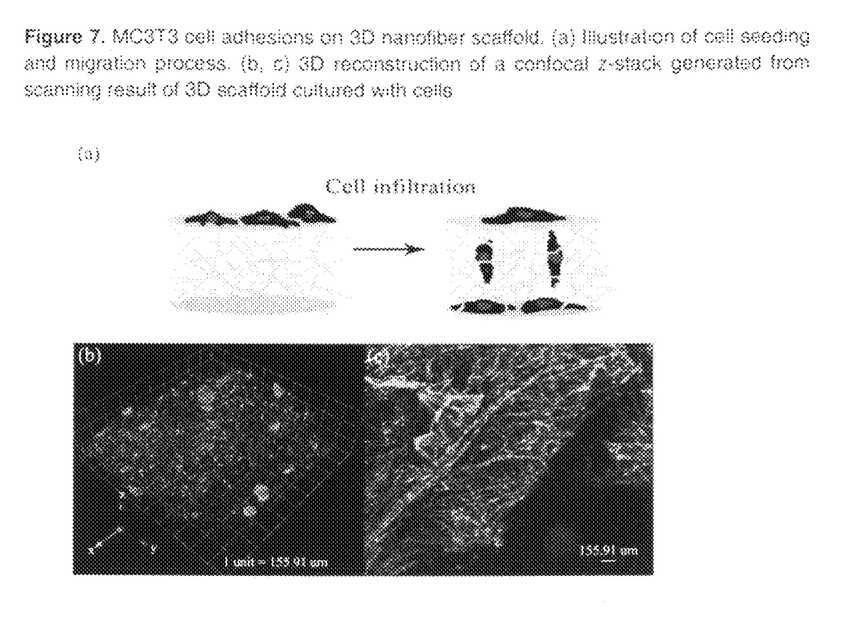
FIG. 7. MC3T3 cell adhesions on 3D nanofiber scaffold. (a) Illustration of cell seeding and migration process. (b, c) 3D reconstruction of a confocal z-stack generated from scanning result of 3D scaffold cultured with cells.

As shown in FIG. 7, cells seeded on 3D nanofibers scaffold migrate into the internal fibrous architecture and fully populated in the central region with depth of about 450 μm, as shown in FIG. 7 (b). We found cells were adhering to the internal nanofibers network and migrated deeply into the nanofiber scaffold, as shown in FIG. 7 (c). The appropriate pore size and higher interconnectivity of 3D nanofiber scaffold allows cells to adhere and penetrate.

Example 8

Growth of MC3T3 Cells on PCL Nanofibers Prepared with Different Needle Movement

Figure 8:
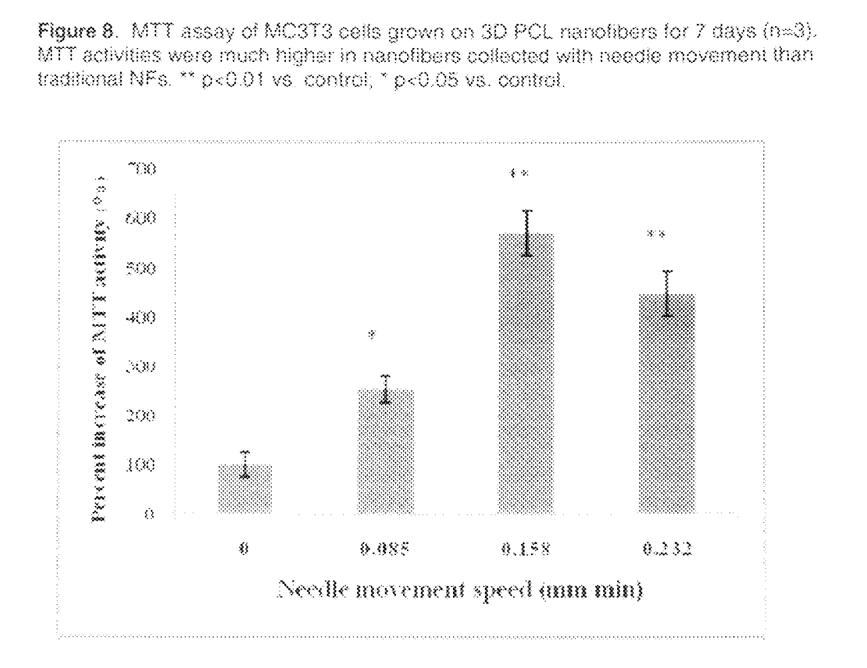
FIG. 8. MTT assay of MC3T3 cells grown on 3D PCL nanofibers for 7 days (n=3). MIT activities were much higher in nanofibers collected with needle movement than traditional NFs. ** $p<0.01$ vs. control; * $p<0.05$ vs. control.

We investigated the effects of nanofiber scaffolds with different microstructures on the infiltration and growth of MC3T3 cells. We prepared PCL nanofiber structures by programming the speed of collector surface needle movement at 0, 0.085, 0.158 and 0.232 mm/min. Results of the MTT assay (FIG. 8) showed that MC3T3 cells cultured on PCL nanofiber structures collected on a moving needle collector had a significant higher cell growth (2.5-5.7-fold) than that of cells cultured on nanofiber scaffolds without needle movement. The cell growth rate is very sensitive to the speed of needle movement and the highest cell growth was observed on nanofiber scaffolds with the setting of needle moving speed at 0.158 mm/min. The reduction of cell growth at slower (0.085 mm/min) or faster (0.232 mm/min) needle movement suggested that the presence of too small or too large spaces within nanofiber matrix might lead to the inferior cell adhesion and/or growth.

It was shown that the loosely packed nanfifiber network structure provides a better host environment for cellular infiltration and growth than the traditional nanofiber scaffolds. Histology analysis showed that MC3T3 cells on the traditional nanofiber scaffolds did not infiltrate below the most superficial layer, whereas cells on the 3D nanofiber scaffolds (collected on needle movement) gradually infiltrated deep into the scaffold. Cells were presented throughout the scaffold at a depth of 300 um from the surface. Our data demonstrates the loosely packed NF network structure provide a better host environment for cellular infiltration and growth than the traditional NF scaffolds.

BRIEF DESCRIPTION OF THE FIGURES

FIG. 2 Multiple rounds (5, 10 and 20) for building 3D nanofibers on automatic nanofiber collector FIG. 3 Preparation of 3D nanofiber composite scaffold by co-electrospinning. The electrospun nanofiber mesh could wrap granules, cells, nanotubes by loading of biomaterials simultaneously or separately during electrospinning. Formed nanofiber composites can be used to fill the defect areas of bone or other tissues. Alternatively, various types of tissue scaffolds with desired shape can be made by compressive modeling or other molding technology for tissue repair.

What is claimed:

1. An automatic nanofiber collector device for use with an electrospinning device comprising
    (1) a collector platform;
    (2) a non-conductive device used to fix the automatic nanofiber collector device;
    (3) a micro-controller;
    (4) A plurality of electro-conductive needles aligned perpendicular to the collector platform wherein the tips of said electro-conductive needles pierce though the collector platform such that the plurality of needle tips are at the same or different heights relative to the collector platform; wherein the opposite ends of said electro-conductive needles are wired and attached to said microcontroller; said microcontroller is programmed to control the movement and speed of said electro-conductive needles; wherein said movement is perpendicular to the collector platform such that a corona discharge is formed during electrospinning when the heights of said needle tips are varied, enabling the gradual build-up of electrospun nanofibers on said collector device.

2. The automatic nanofiber collector device of claim 1, wherein the length of the electro-conductive needles ranges from 1 mm to 1 m and the diameter of the electro-conductive needles ranges from 0.01 um to 10 mm, and wherein the electro-conductive needles are either the same or different in their length and diameter.

3. The automatic nanofiber collector device of claim 1 wherein the speed of the electro-conductive needle is over 0.1 mm/min, the movement of the needle is composed of a round wherein each round comprises at least a relative increase in the height of the needle tip, a relative decrease in the height of the needle tip, and a period wherein the height of the needle tip is unchanged; and wherein the build-up of the electrospun nanofibers comprise at least 10 rounds.

4. The automatic nanofiber collector device of claim 1 further comprising a spinneret wherein a polymeric solution is injected out of the spinneret to produce a fibrous jet and wherein the distance between the needle tips and the distal end of the spinneret varies by controlling the height of the needle tips.

5. The automatic nanofiber collector device of claim 1 wherein the number of electro-conductive needles and pattern of electro-conductive needles pierced through the collector platform are adjustable.

\* \* \* \* \*